United States Patent [19]

Nelson et al.

[11] Patent Number: 4,665,057

[45] Date of Patent: May 12, 1987

[54] NUTRIENT MONOESTERS

[76] Inventors: Deanna Nelson, 9025 Moody Ave., Morton Grove, Ill. 60053; Bruce Rowe, 6427 N. Newgard, Chicago, Ill. 60626

[21] Appl. No.: 477,791

[22] Filed: Mar. 22, 1983

[51] Int. Cl.$^4$ ............................................. A61K 31/70
[52] U.S. Cl. ...................................... 514/23; 514/546; 514/552; 536/115; 536/119
[58] Field of Search ...................... 424/180, 311, 312; 536/119, 115; 514/23, 552, 546

[56] References Cited

U.S. PATENT DOCUMENTS

| | | | |
|---|---|---|---|
| 2,357,077 | 8/1944 | Brown | 424/312 |
| 3,849,554 | 7/1969 | Winitz | 424/180 |
| 3,952,107 | 4/1976 | Shibata | 424/311 |
| 3,963,699 | 6/1976 | Rizzi et al. | 424/180 |
| 4,005,195 | 1/1977 | Jandacek | 424/312 |
| 4,036,991 | 7/1977 | Stiefel | 424/365 |
| 4,048,202 | 9/1977 | Beck et al. | 424/312 |
| 4,148,887 | 4/1979 | Smith | 424/180 |

Primary Examiner—Johnnie R. Brown
Assistant Examiner—Elli Peselev

[57] ABSTRACT

Synthetic monesters are employed as calorie sources for parenteral or enteral nutrition. The monoesters are hydrolyzed and respired by the body and offer the advantage of high calorie density when compared to conventional or other synthetic calorie sources.

28 Claims, No Drawings

NUTRIENT MONOESTERS

BACKGROUND OF THE INVENTION

This invention relates to the field of nutrition, and more particularly to parenteral nutrition via peripheral veins.

Total parenteral nutrition (TPN) is a recent advance in the maintenance of patients having an impaired gastrointestinal capacity. Such patients may have lost the use of a large portion of their intestinal tract, either permanently due to surgical intervention as may be required in cancer or Crohn's disease, or temporarily as a result of chemotherapeutic drugs or in the treatment of diverticulitis. Objectives of TPN include administering all of the patient's requirements of calories and essential nutrients directly into the circulatory system, bypassing the digestive tract entirely, or administering nutrients to the remnant digestive tract in a form that will provide as much nutrition as possible without injuring either the circulatory system or the intestines.

A major difficulty in TPN has been the sensitivity of the intestines or vasculature to contact with nutrient solutions having high osmolarity. To date, it has been necessary to use such highly concentrated solutions because at lower concentrations the nutrient solutions supply insufficient calories before exceeding the patient's ability to deal with excess diluent. Generally, a patient must receive at least 2500 ml daily of a 20% glucose solution to reach the 2000 minimum calories required, and caloric requirements can be greater in many stressed patients.

Attempts to deal with this problem have included infusing the solution via a central venous catheter. A catheter is threaded from a peripheral vein in an arm or a leg, for example, into the vena cava. Highly concentrated nutrient solutions can be passed through the catheter into the large volume of central venous blood, where rapid dilution of the solution obviates vascular injury and reduces local hemolysis. Central venous catheters, however, among other disadvantages require a special procedure to insert. It would be safer and considerably more convenient if parenteral nutrition could be administered via a peripheral vein.

Calorie sources for infusion which are alternate or supplemental to glucose, amino acids or lipid emulsions have been previously suggested or disclosed. See Birkhahn, R. et al., "J. Par. Ent. Nutr." 5(1):24–31 (1981); Birkhahn, R. et al., "Am. J. Clin. Nutr.", 30: 2078–2082 (1977); Birkhahn, R. et al., "Am. J. Clin. Nutr." 31:436–441 (1978); Birkhahn, R. et al., "J. Nutr." 109:1168–1174 (1979); Birkhahn, R. et al., "J. Par. Ent. Nutr." 3(5):346–349 (1979); LeVeen, H., "Am. J. Dig. Dis." 17:20 (1950); LeVeen, H., "Am. J. Clin. Nutr." 5:251 (1957) and Milner, U.S. Pat. No. 3,928,135. None of the compounds have proven entirely satisfactory, especially for peripheral vein infusion. The principal difficulties have included insufficient calorie density for peripheral infusion, incomplete metabolism of the compounds, toxic metabolites, side effects, and insufficient water solubility.

Accordingly, the objectives of this invention include:

(a) providing compounds for parenteral or enteral nutrition which are biologically available;

(b) providing compounds having a biologically available caloric content in considerable excess of glucose;

(c) providing compounds which are nontoxic to the vasculature, the intestines and the cellular elements of the blood, in particular compounds which exhibit insufficient surfactant properties to hemolyze or otherwise damage erythrocytes;

(d) providing compounds which can be dissolved in solutions to yield infusates having improved calorie density;

(e) providing and administering to patients the above compounds in conventional parenteral solution containers along with other nutrients such as vitamins, electrolytes, trace metals and amino acids; and (f) providing compounds which are hydrolyzed by the tissues or intestinal flora to substrates of oxidative metabolism.

These and other objects will be apparent from consideration of this specification as a whole.

SUMMARY OF THE INVENTION

The foregoing objects are achieved by enteral or parenteral administration of novel compounds having the formula

AOOCR wherein

A is the residue of a nontoxic, biologically available normal or branched chain aliphatic group containing at least one hydroxyl substituent and one or more oxy or additional hydroxyl substituents; and —OOCR is the residue of a fatty acid having less than 7 carbon atoms, an alpha-keto carboxylic acid, or a fatty acid having an even number of carbon atoms and being substituted with oxy or hydroxyl at the 2 carbon position, with hydroxyl at the 3 carbon position, and/or with oxy or hydroxyl at any odd numbered carbon thereafter, provided that no more than 6 consecutive carbon atoms remain unsubstituted with oxy or hydroxyl;

provided that when —OOCR is the residue of a fatty acid having less than 7 carbon atoms, then A is not a residue of glycerol.

The resulting monoesters are highly water soluble and contain improved calorie density. They are nontoxic upon parenteral administration in nutritional doses and are hydrolyzed in the body.

DETAILED DESCRIPTION OF THE INVENTION

The fundamental reasoning underlying this invention is that medium or long chain fatty acids, when hydroxylated in the fashion provided herein and esterified to nutrient polyols, provide a high calorie compound that is readily hydrolyzed in the body to low molecular weight oxidative intermediates or to low molecular weight substances which are readily converted to such intermediates.

"Biologically available" as that term is used herein means that the monoester and its ester hydrolysis products are substantially oxidized in the body to $CO_2$, $H_2O$ or other low molecular weight products excreted as ordinary byproducts of tissue respiration.

Certain normal or branched chain aliphatic groups containing at least two hydroxyl substituents are widely recognized as toxic, e.g. ethylene glycol, propylene glycol, 1,2-butanediol, 1,4-butanediol. These substances will be apparent to those skilled in the art, and are not to be employed as components in assembling the monoesters herein. "Nontoxic" monoesters or hydrolysis products are those which exhibit an $LD_{50}$ in mice at greater than 1 g/kg body weight upon continuous administration by the route contemplated for the monoester, e.g. oral or parenteral.

The "A" radical generally falls into several representative classes. The first class is the residues of saccharides, including the monosaccharide pentoses or hexoses and their corresponding ketoses. Monosaccharides are preferred as they are most readily hydrolyzed by the body upon parenteral administration. Suitable monosaccharides may be reducing sugars such as glucose or fructose or nonreducing sugars such a sorbose or mannose. The corresponding sugar alcohols such as sorbitol or mannitol also may be employed, although these are not preferred because their rate of biological utilization is not as high as monosaccharides. The monosaccharide or sugar alcohol is esterified at any of the hydroxyl groups of the monosaccharide or sugar alcohol, but generally the 1, 5 or 6 positions are preferred.

Group "A" also may be the residue of a nontoxic, short chain biologically available normal aliphatic diol or triol. Exemplary "A" groups of this class are $(CH_2OH)_2CH-$, $CH_2(OH)CH(OH)CH_2-$ and $CH_3CH(OH)CH_2CH_2-$, with the 1-or 3-glyceryl ester being most preferred.

The group —OOCR will contain about from 4 to 10 carbon atoms, ordinarily 4 to 6, and is preferably normal. The number of hydrophilic substitutents should be directly proportional to the number of carbon atoms, with a greater proportion in the case of a branched chain carbon skeleton. —OOCR groups include, hexanoic acid, alpha keto acids and hydroxylated fatty acids , the latter most being preferred. Representative —OOCR groups include

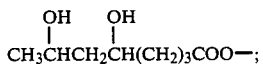

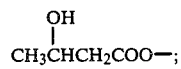

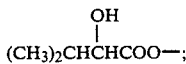

Preferably, —OOCR is 5, 7-dihydroxyoctanoic acid or hexanoic acid. Hexanoic acid is preferably esterified with monosaccharides.

Selection of groups A and R will have the objective of optimizing several characteristics of the resulting monoester. First, the monoester must be soluble at room temperature in substantially neutral aqueous solutions, e.g. those having a pH of about from 5.5 to 7.5. Thus, radicals having alkylene residues of greater than $C_4$ will need to be used sparingly to improve the water solubility of the monoesters. However, even poorly soluble monoesters can be employed as supplements to other nutrients or other more soluble polyesters, or their solubility may be increased by the use of a cosolvent such as ethanol. Generally, the monoesters and their hydrolysis products should have a solubility of greater than about 3 mole percent in water at room temperature.

The second characteristic to be optimized is biological availability, as defined briefly above. The monoesters must be hydrolyzed in the body after infusion or ingestion, although the manner in which this occurs is not as important as the fact that it does. Monoesters should be selected which are susceptible to solvolysis or hydrolysis upon contact of the monoester with components such as hydrogen ions present in the blood. Esters selected for susceptibility to solvolysis will have —OOCR groups with polar functionalities at the 3 or 5 positions.

Most likely, hydrolysis is the primary result of enzymatic action in blood cells, plasma and body tissues and organs. Also, enzymatic hydrolysis by intestinal flora will occur after enteral administration. Hydrolysis will be dependent upon many factors. For example, some monoesters may be optimal in the TPN of patients with gastrointestinal disease while the same monoesters might not be optimal for a patient with liver disease if the monoester is principally hydrolyzed by liver enzymes. Thus, the clinician must use some discretion in selecting monoesters for optimal biological availability. The experimental method for the selection will be relatively straightforward, however. The ultimate criterion is stabilization of weight loss, or a gain in weight, in the patient being treated. A more immediate assay for availability would be to determine plasma increases in representative monoester hydrolysis products, e.g. glycerol. In such a case a monoester is biologically available if it is hydrolyzed in the body at a rate sufficient to supply nutrition. This rate may be quite low, however, if the monoester is to serve as a supplementary nutrient.

The monoester must be nontoxic as defined above. However, it may be of value to select monoesters on the basis of more specific data than lethal dose in mice. For example, the influence of the monoesters on lipases and esterases in blood and tissues can be readily determined by assaying the particular enzyme activity on a given, usually normal physiological, substrate for the enzyme in the presence or absence of the monoester or its hydrolysis products. It should be noted that competitive, reversible inhibition of existing enzyme systems by the monoesters or their hydrolysis products is not disadvantageous. In fact, one feature of this invention is that hydrolysis of the monoesters is in part dependent upon the unexpectedly fortuitous existence of unfastidious esterases which ordinarily hydrolyze other substrates in the body. The administration of the monoesters may result in some transient inhibition of these normal hydrolytic activities, but induction of greater amounts of the enzymes in question soon will overcome any such inhibition. The impact of the monoesters on existing in vivo hydrolyzing systems is lessened by the use of a multiplicity of monoesters in the infusate, e.g. a mixture of monosaccharide and glycerol esters of fatty acids and their oxy or hydroxyl derivatives.

Monoesters should be chosen which can be autoclaved with minimal thermal hydrolysis and without other rearrangements such as polymerization. This will be an objective if the monoesters are to be infused parenterally, but will not be of concern where the monoesters are to be administered enterally and sterile administration is not required. If the monoesters are thermally unstable they may be sterilized by other known methods, for example, sterile filtration. The monoesters of this invention may be autoclaved in solution with amino acids.

Representative monoesters which are contemplated in the practice of this invention are described in Table I.

TABLE I

1. CH$_2$(OH)CH(OH)CH$_2$OOC(CH$_2$)$_3$CH(OH)CH$_2$CH(OH)CH$_3$
2. CH$_2$(OH)CH(OH)CH$_2$OOCCH$_2$CH(OH)CH$_3$
3. CH$_3$CH(OH)CH$_2$CH$_2$OOCCH$_2$CH(OH)CH$_3$

4.  $$CH_2(OH)CH(OH)CH_2OO\overset{O}{\overset{\|}{C}}CCH_2CH_3$$

5. CH(CH$_2$OH)$_2$OOC(CH$_2$)$_3$CH(OH)CH$_2$CH(OH)CH$_3$
6. CH$_3$CH(OH)CH$_2$CH$_2$OOC(CH$_2$)$_3$CH(OH)CH$_2$CH(OH)CH$_3$
7. CH$_3$CH[OOCCH$_2$CH(OH)CH$_3$]CH$_2$CH$_2$OH

8.  $$CH_3CH(OH)CH_2CH_2OO\overset{O}{\overset{\|}{C}}CCH_2CH_3$$

9.  ```
    ┌─CHOOC(CH₂)₃CH(OH)CH₂CH(OH)CH₃
    │  HCOH
    O  HOCH
    │  HCOH
    └─CH
       CH₂OH
    ```

10. ```
    ┌─CHOH
    │  HCOH
    O  HOCH
    │  HCOH
    └─CH
       CH₂OOC(CH₂)₃CH(OH)CH₂CH(OH)CH₃
    ```

11. ```
    ┌─CHOH
    │  HCOH
    O  HOCH
    │  HCOH
    └─CH     O
             ‖
       CH₂OOCCH(CH₃)CH₂CH₃
    ```

12. CH$_2$(OH)CH(OH)CH$_2$OOCCH(OH)CH(CH$_3$)$_2$

13. ```
    ┌─CH₂OOC(CH₂)₃CH(OH)CH₂CH(OH)CH₃
    │  HCOH
    │  HOCH
    O  HCOH
    │
    └─CH₂
    ```

The monoesters have the principal advantage over glucose in having an extremely high available calorie density. The following Table 2 demonstrates the high energy density of the monoesters in comparison with other calorie sources.

TABLE 2

| Compound | Mole Weight | ATP* | Kcal/Mol | Parenteral Solution for TPN+ mM |
|---|---|---|---|---|
| glycerol | 92 | 19 | 228 | 2193 |
| glucose | 180 | 38 | 456 | 1096 |
| 1,3-butanediol | 90 | 31 | 372 | 1344 |
| monobutyrin# | 162 | 48 | 923 | 856 |
| glyceryl 5,7-dihydroxyoctanoate | 250 | 78 | 936 | 534 |
| glucose monohexanoate | 278 | 84 | 1008 | 496 |
| glucose 5,7-dihydroxyoctanoate | 338 | 97 | 1164 | 429 |

Birkhahn et al. "J. Par. Ent. Nutr." 5(1):24 (1981).
*calculated adenosine triphosphate generated upon complete respiration of the compound.
+0.5 Kcal/ml solution The monoesters described herein are useful in stabilizing or increasing patient weight, reducing nitrogen loss (particularly the alpha-keto carboxylic acid esters) and effecting other metabolic and physiological improvement in the clinical state of the patient.

For parenteral administration, the selected monoester or mixture of monoesters is dissolved in an aqueous solution at the desired concentration. This concentration may be that which is intended for use, e.g. about from 5 to 20 mole percent, or may be more concentrated, e.g. about from 10 up to 50 mole percent or the saturation solubility limit of the monoester. Concentrated solutions are maintained at the greater concentration to enhance the monoester stability during autoclaving or storage. Such solutions then are diluted to the desired administration concentration at some convenient point before use. If necessary, the monoester need not be dissolved in an aqueous solution at all until reconstitution before administration. This, however, is not as commercially desirable as supplying a ready-to-use solution.

The monoester solution frequently will be mixed with other nutrients or with drugs. Such other nutrients may include nitrogen sources such as amino acids, essential fatty acids such as linoleic or linolenic acid, vitamins, minerals, and electrolytes including trace elements. Other calorie sources such as carbohydrates or lipids will not ordinarily be needed. The amino acids are mixed with the monoester prior to or after sterilization. A mixture of essential amino acids nutritionally balanced according to the Rose proportions will ordinarily be sufficient, although nonessential amino acids may be included. The proportions may be adjusted for special disease states, e.g., inborn errors of metabolism, in accord with known practice. Supplemental nutrients also will be selected to avoid adverse effects on the monoesters during sterilization and/or storage, e.g. accelerated hydrolysis. The pH may range about from 5.5 to 7.5. Other conventional additives such as antioxidants, buffers and the like may be included as well.

The solutions are packaged in conventional parenteral solution containers, either glass or thermoplastic flexible bags. Such containers are sterile sealed and will contain means for communicating with the patient's circulation, either alone or in concert with other devices. Typically, the means for communicating with the patient's circulation will be a frangible member associated with the container which is adapted to enter into fluid communication with an administration set. Such sets also are well known.

The solutions usually are parenterally administered by infusion into a peripheral vein. The monoester concentration is not critical. It should not be so low as to introduce undue amounts of water into the patient, nor so high as to cause peripheral vascular irritation. Generally an osmolarity below about 600 mOsm. is satisfactory for peripheral parenteral infusion. Less advantageously, the solution may be infused through a central venous catheter. The solutions are infused at a rate sufficient to maintain the nutritional status of the patient in concert with the intake of other nutrients. Infusion will be ordinarily about from 25 to 40 Kcal/Kg patient weight/day, but the amount administered parenterally will depend upon the patient's oral intake of monoester or other nutrients.

The monoesters herein can be taken orally, and they have the advantage of a higher energy content than glucose so are less likely to cause diarrhea or other intestinal distress at a given Kcal dose when compared to glucose. The monoesters, alone or in combination with other nutrients as described above or with drugs, can be taken by gastric tube or as a component of ordinary meals. Since the monoesters are to function as nutrients they are supplied in quantities sufficiently high to provide greater than 20%, preferably greater than 50% of the calories required by the patient.

The monoesters may be made by modifications of known synthetic methods.

The invention will be more fully understood from a study of the following examples.

EXAMPLE 1

Preparation of Glyceryl 5,7-Dihydroxyoctanoate 5,7-dihydroxyoctanoic acid delta-lactone was prepared in several steps from cyclopentanone and 2-benzyloxy-1-chloropropane. Thus, alkylation of cyclopentanone was effected by treatment with sodium hydride in tetrahydrofuran (THF) solution to generate the alpha-anion, followed by the dropwise addition of a THF solution of 2-benzyloxy-1-chloropropane. Reaction workup yielded 2-(2-benzyloxy-1-propyl) cyclopentanone. This ketone was treated with peroxy trifluoroacetic acid under Baeyer-Villiger conditions to give the 7-benzyl ether of 5,7-dihydroxyoctanoic acid gamma-lactone. The benzyl group was removed by catalytic hydrogenation, yielding 5,7-dihydroxyoctanoic acid delta-lactone.

Esterification was accomplished as follows: A solution of 9.2 g of glycerol and 15.8 g of 5,7-dihydroxyoctanoic acid delta-lactone in 100 ml dioxane containing 0.1 g sodium hydride was heated at reflux for 18 hours. The solution was cooled to room temperature, 1 ml of H2O was added, and volatile materials were removed in vacuo. The residual oil was taken up in chloroform, washed with a minimum volume of water and dried over anhydrous MgSO4. After filtration, the chloroform solution was concentrated to a colorless oil (23.8 g), which was identified as glyceryl 5,7-dihydroxyoctanoate.

EXAMPLE 2

Preparation of Glucose Monohexanoate

The method of Pfander and Laederach [H. Pfander and M. Laederach, Carbohyd. Res. 99(2), 175–79 (1982)] was used. 1-Hexanoylimidazole was prepared by stirring 2 equivalents of imidazole with 1 equivalent hexanoyl chloride in toluene solution. The mixture was filtered and concentrated to a low-melting solid. This product, 1-hexanoylimidazole, was further purified by distillation.

The imidazole derivative (1 equivalent) was treated with 2 equivalents of B-D-glucose and a catalytic amount of sodium hydride in pyridine at room temperature. After stirring for 24 hours the solution was concentrated, chloroform was added, and the precipitate was removed by filtration. The filtrate was concentrated to a colorless solid, which was further purified by chromatography. Yields of product, 1-0-hexanoyl-B-D-glucopyranose, ranged from 20–60%, depending on the precautions taken to maintain anhydrous reaction conditions.

EXAMPLE 3

The compounds of Examples 1 and 2 were each dissolved in water to a concentration calculated to yield 0.5 Kcal/ml. 200 ml of each of the solutions were prepared by sterile filtration. The sterilized solutions were continuously infused into rats at a rate of 120 ml/Kg/day. The rats were able to metabolize the monoesters and to subsist on them in the absence of oral food intake.

We claim:

1. A composition for enteral or parenteral nutrition comprising a nutritionally effective amount of a compound of the formula

AOOCR wherein
A is the residue of a nontoxic, biologically available normal or branched chain aliphatic group having one to four carbon atoms and containing one or two hydroxyl substituents, or a monosaccharide selected from the group consisting of glucose, fructose, or mannose or of sorbitol; and
—OOCR is a fatty acid having four to ten carbon atoms and being substituted with oxy and/or hydroxyl, provided that no more than 6 consecutive carbon atoms remain unsubstituted with oxy or hydroxyl;
provided that when —OOCR is the residue of a fatty acid having less than 7 carbon atoms then A is not a residue of glycerol.

2. The composition of claim 1 wherein A is the residue of glucose, fructose or mannose.

3. The composition of claim 1 wherein —OOCR is an alpha-hydroxy carboxylic acid residue.

4. The composition of claim 1 wherein —OOCR is a 3-or a 5, 7-hydroxy substituted fatty acid residue.

5. The composition of claim 1 wherein —OOCR is

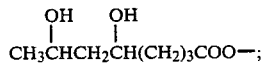

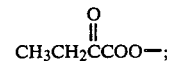

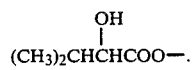

6. The composition of claim 1 wherein A is CH2(OH)CH(OH)CH2-.

7. The composition of claim 2 wherein A is the residue of glucose or fructose.

8. The composition of claim 1 where A is the residue of sorbitol.

9. The composition of claim 1 wherein the compound is in an aqueous solution in a concentration of about from 5 to 15 mole percent.

10. The composition of claim 1 which is essentially free of biologically active contaminants.

11. The composition of claim 1 sealed in a container having means for making fluid communication with the circulation of a patient.

12. The composition of claim 1 which is sterile and sterile sealed in a flexible, thermoplastic container.

13. The composition of claim 1 wherein the composition also contains amino acids.

14. The composition of claim 13 wherein the amino acids are a nutritionally balanced mixture of essential amino acids.

15. The composition of claim 1 wherein the composition also contains a monosaccharide.

16. The composition of claim 1 comprising mixtures of two or more of the compounds.

17. The composition of claim 1 having an osmolarity less than about 600 mOsm.

18. The composition of claim 1 which is essentially free of water insoluble substances.

19. The composition of claim 1 wherein the compound is glucose monohexanoate.

20. A method for the nutritional support of a patient receiving otherwise inadequate nutrition, comprising administering to the patient a solution of the composition of claim 1.

21. The method of claim 20 wherein the solution is administered by infusion into a peripheral vein.

22. The method of claim 20 wherein —OOCR is

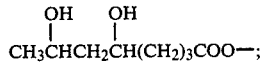

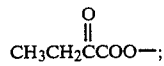

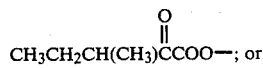

or

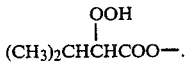

23. A composition for parenteral nutrition comprising a nutritionally effective amount of a compound of the formula

AOOCR wherein
A is the residue of a nontoxic, biologically availiable normal or branched chain aliphatic group having one to four carbon atoms and containing one or two hydroxyl substitutents; and
—OOCR is a fatty acid having four to ten carbon atoms and being substituted with oxy or hydroxyl, provided that no more than 6 consecutive carbon atoms remain unsubstituted with oxy or hydroxyl;
provided that when —OOCR is the residue of a fatty acid having less than 7 carbon atoms then A is not a residue of glycerol.

24. A method for the nutritional support of a patient receiving otherwise inadequate nutrition, comprising administering to the patient a solution of the composition of claim 23.

25. The composition of claim 1 wherein the compound is thermally stable and can be autoclaved.

26. The composition of claim 23 wherein the compoud is thermally stable and can be autoclaved.

27. A method for providing greater then 20% of the calories required by a patient comprising parenterally administering a nutritionally effective amount of a composition comprising a water-soluble compound of the formula

AOOCR wherein
A is the residue of a nontoxic, biologically available normal or branched chain aliphatic group containing one hydroxyl substituent and one or more oxy or additional hydroxyl substituents, or of a monosaccharide selected from the group consisting of glucose, fructose, or mannose or of sorbitol; and
—OOCR is the residue of a fatty acid having four to ten carbon atoms and being substituted with oxy and/or hydroxyl, provided that no more than 6 consecutive carbon atoms remain unsubstituted with oxy or hydroxyl;
provided that when —OOCR is the residue of a fatty acid having less than 7 carbon atoms then A is not a residue of glycerol.

28. A method for providing greater than 20% of the calories required by a patient comprising parenterally administering a nutritionally effective amount of a composition comprising a water-soluble compound of the formula

AOOCR wherein
A is the residue of a nontoxic, biologically available normal or branched chain aliphatic group having one to four carbon atoms and containing one or two hydroxyl substitutents; and
—OOCR is a fatty acid having four to ten carbon atoms and being substituted with oxy or hydroxyl, provided that no more than 6 consecutive carbon atoms remain unsubstituted with oxy or hydroxyl;
provided that when —OOCR is the residue of a fatty acid having less than 7 carbon atoms then A is not a residue of glycerol.

* * * * *